United States Patent
Bone

(10) Patent No.: US 10,456,028 B2
(45) Date of Patent: *Oct. 29, 2019

(54) APPARATUS FOR USE IN THE MEASUREMENT OF MACULAR PIGMENT OPTICAL DENSITY AND/OR LENS OPTICAL DENSITY OF AN EYE

(71) Applicant: Guardion Health Sciences, LLC, San Diego, CA (US)

(72) Inventor: Richard Bone, Miami, FL (US)

(73) Assignee: Guardion Health Sciences, LLC, San Diego, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 15/346,010

(22) Filed: Nov. 8, 2016

(65) Prior Publication Data

US 2017/0231486 A1 Aug. 17, 2017

Related U.S. Application Data

(63) Continuation-in-part of application No. 14/377,929, filed as application No. PCT/US2013/025600 on Feb. 11, 2013, now Pat. No. 9,486,136.

(60) Provisional application No. 61/597,654, filed on Feb. 10, 2012.

(51) Int. Cl.
| | |
|---|---|
| *A61B 3/02* | (2006.01) |
| *A61B 3/00* | (2006.01) |
| *A61B 3/06* | (2006.01) |
| *A61B 3/14* | (2006.01) |
| *G01J 3/02* | (2006.01) |
| *G01J 3/10* | (2006.01) |

(52) U.S. Cl.
CPC .............. *A61B 3/02* (2013.01); *A61B 3/0025* (2013.01); *A61B 3/0058* (2013.01); *A61B 3/0075* (2013.01); *A61B 3/066* (2013.01); *A61B 3/14* (2013.01); *G01J 3/0254* (2013.01); *G01J 3/10* (2013.01)

(58) Field of Classification Search
CPC .. A61B 3/02; A61B 3/14; A61B 3/066; A61B 3/0058; A61B 3/0025; A61B 3/0075; A61B 3/0008; G01J 3/10; G01J 3/0254; G01J 1/0451; G01J 1/0252; G01J 1/0266; G02B 21/0096
USPC ........................................ 351/221, 206, 243
See application file for complete search history.

(56) References Cited

U.S. PATENT DOCUMENTS

| | | | |
|---|---|---|---|
| 4,120,582 | A | 10/1978 | De Vries et al. |
| 6,017,122 | A | 1/2000 | Bone et al. |
| 6,244,709 | B1 | 6/2001 | Vayntraub |
| 2005/0010115 | A1 | 1/2005 | Bone et al. |
| 2006/0227290 | A1 | 10/2006 | Murray et al. |

(Continued)

OTHER PUBLICATIONS

Wooten et al., A Practical Method for Measuring Macular Pigment Optical Density. IOVS, Oct. 1999, vol. 40, No. 11, p. 2481-2489.

*Primary Examiner* — Evan P Dzierzynski
*Assistant Examiner* — Alberto J Betancourt
(74) *Attorney, Agent, or Firm* — Lewis Kohn & Walker LLP; David M. Kohn; Kari Moyer-Henry

(57) ABSTRACT

An apparatus for use in the measurement of the optical density of macular pigment in the human eye, and an apparatus for the use in measuring the lens optical density of a human eye. The apparatus is particularly applicable to flicker photometers, which are used to measure the macular pigment in the human eye.

22 Claims, 6 Drawing Sheets

(56) References Cited

U.S. PATENT DOCUMENTS

2007/0078349 A1\* 4/2007 Ferguson ............ A61B 5/0059
600/476
2011/0009926 A1 1/2011 Howard
2011/0211161 A1 9/2011 Gierhart et al.

\* cited by examiner

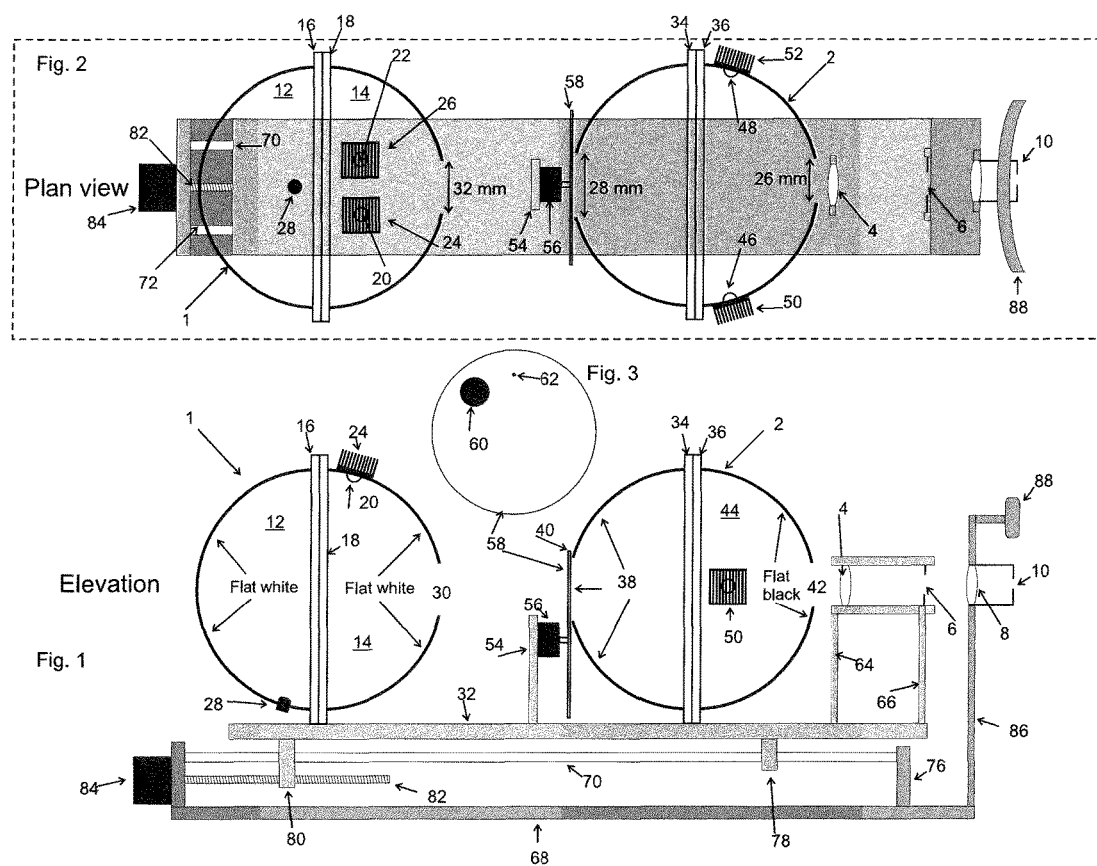

MAPCAT SYSTEM BLOCK DIAGRAM

MAPCAT LED INTENSITY CONTROL DIAGRAM

MAPCAT LED INTENSITY MEASUREMENT TIMING DIAGRAM

APPARATUS FOR USE IN THE MEASUREMENT OF MACULAR PIGMENT OPTICAL DENSITY AND/OR LENS OPTICAL DENSITY OF AN EYE

RELATED APPLICATIONS

This application is a Continuation-in-Part claiming priority from U.S. National Stage patent application Ser. No. 14/377,929 filed Aug. 11, 2014, now U.S. Pat. No. 9,486,136 which claims priority under 371 to International Patent Application No. PCT/US13/25600 filed Feb. 11, 2013, which claims priority from U.S. Provisional Application No. 61/597,654, filed on Feb. 10, 2012, the contents of which are hereby incorporated by reference herein.

FIELD OF THE INVENTION

This invention relates to apparatus for use in the measurement of the optical density of macular pigment in the human eye, and to apparatus for the use in measuring the lens optical density of a human eye.

BACKGROUND OF THE INVENTION

The invention is particularly applicable to flicker photometers, which are used to measure the macular pigment in the human eye.

Macular pigment is the yellow pigment situated in the central portion of the human retina. The absorption spectrum for the pigment has a peak for light of a wavelength of 460 nm, and is zero for light of a wavelength of 540 nm, so that the pigment absorbs significant amounts of the shorter wavelength light whilst having little or no effect on light of the longer wavelength.

The highest concentrations of macular pigments are to be found in the region of the retina, the macula lutea (hereinafter referred to as the macula), which has a very high number density of cone receptors, and is coupled to a disproportionately large area of the visual cortex, giving that region a high degree of visual acuity. In fact, the macular pigment lies on a portion of the retina which corresponds to the center of the field of view of a subject (through that eye).

It has been proposed that the macular pigment protects the retina against harmful effects of short wavelength radiation, and that the pigment indeed provides protection against age related macular degeneration (AMD), a disease that leads to vision loss in the center of the visual field. Accordingly, much effort has been devoted to the noninvasive measurement of the density of macular pigment in the human eye.

To that end, a flicker photometer projects green and blue light (respectively of wavelengths of typically 540 nm and 460 nm) into a subject's eye so that the subject perceives a flickering stimulus in the center of his or her field of view. The subject can then adjust the intensity of one of the colors of light, typically the blue light. If an appropriate flicker frequency has been selected initially, the subject will be able to select an intensity of the blue light which is such that the subject perceives no, or a minimum amount of, flickering.

The intensity of the blue light is then determined, and this value can be used in calculating the macular pigment density. However, the selected intensity may be influenced by yellowing in the lens of the eye under examination, and this can vary from one subject to the next.

U.S. Pat. No. 5,936,724 and U.S. Pat. No. 6,017,122 show a flicker photometer in which the possible contribution of yellowing of the lens is eliminated by having the subject look at an offset mark and then repeating the intensity adjustment process until the perceived flicker of the stimulus, which is now in the subject's peripheral field of view, is minimized or eliminated.

However, this second type of measurement is found by some subjects to be a challenging task that often requires a period of training. One possible reason for this is that many subjects may find it difficult to concentrate on a stimulus in their peripheral field of view whilst resisting the urge to shift their view so that they are looking directly at the stimulus (which would then once again be on the macula).

SUMMARY OF THE INVENTION

According to a first aspect of the invention, there is provided apparatus for use in the measurement of macular pigment optical density in an eye under examination, the apparatus comprising illumination means for illuminating an area with light of a rapidly repeating sequence of different colors, to provide a stimulus for said eye; intensity adjustment means for adjusting the relative intensity of light of at least one of said colors, until any flicker in the stimulus perceived by the eye is minimized or removed; measurement means for determining the intensity of light of said at least one color at which said minimizing or removal of flicker occurs, wherein the apparatus includes size selection means for enabling the size of the stimulus to be selected from either of a small size, in which all or most of the stimulus, in use, falls on the macula of the eye, or a large size, in which the stimulus extends to a portion of the retina of the eye at which there is substantially no macular pigment.

The density of macular pigment affects the measured intensity for the small stimulus, whilst the large stimulus can be used to obtain a measurement that enables the natural yellowing of the eye's lens to be taken into account. The latter measurement does not require that the subject looks at an offset fixation mark. Instead, the subject can look at the same point for both measurements. It has been found that subjects are far more comfortable with the central fixation for both parts of the test, than they are having to fixate on an offset mark for one of the parts of the test.

Preferably, the apparatus includes a viewing element via which, in use, either stimulus is viewed by the eye under examination at a set minimum distance from the illuminated area that provides the stimuli, so that the angle that each stimulus subtends at the eye is controlled or constrained.

In this case, preferably, the small stimulus subtends at an angle of not more than 1.5° at the eye under examination.

Preferably, at least part of the large stimulus subtends at an angle of at least 14° at the eye under examination.

The large stimulus can thus extend to the center of the subject's field of view so that the measurement using the larger stimulus can be taken while the subject is looking directly at the latter. This means that, when the subject adjusts the intensity of light of at least one of the colors to eliminate or minimize flicker in an offset portion of the large stimulus, flickering in the center of the field of the subject's view will remain. It has been found that this task is easier than that of trying to eliminate flicker in a small, peripherally fixated stimulus. Even if the subject's gaze wanders to different points on the large stimulus, the measurement can still be made, because the goal for the subject remains to minimize or eliminate flicker in parts of the stimulus which are not in the centre of the subject's field of view: precise fixation of the subject's eye on the given point is therefore not mandatory for the part of the test that involves the large stimulus.

Preferably, both stimuli are symmetric about a central point. This makes it easier for the subject to keep looking at the same point (i.e. the central point) for both measurements.

In this case, the two stimuli are preferably circular and are concentric with each other.

The viewing element conveniently comprises part of a telescope having a target marking which acts as a fixation point for the user.

Preferably, the apparatus comprises a flicker photometer, the illumination means of which is such that the repeating sequence of colors is an alternating sequence of two colors. Preferably, the two colors are blue and green.

The absorbance spectrum of macular pigment peaks at blue light of a wavelength of 460 nm, but is substantially zero for green light. The pigment therefore affects the subject's perception of blue light, but not the green.

The illumination means may comprise any arrangement of light sources, for example incandescent, fluorescent or electroluminescent that can provide adequately controllable alternating color illumination of the area, and may indeed even include the area. Thus, for example, the illumination means may comprise a color cathode ray tube, LCD or OLED display screen, the stimuli being constituted by images/shapes displayed thereon.

Preferably, however, the illuminating means comprises a blue light source and a green light source which alternately illuminate an area constituted by a light diffusing surface.

Said surface may be a translucent screen in front of the sources, but is preferably an opaque screen which, in use, is illuminated by the sources from the front.

Preferably, the screen comprises an integrating sphere, which conveniently contains said light sources.

The light sources may to advantage comprise a blue LED and a green LED.

These are relatively efficient light sources which generate relatively little waste heat, and emit light over a sufficiently narrow spectrum of wavelength to avoid the need for any color filters to be used with the sources.

Preferably, the apparatus includes a photodetector for measuring the intensity of blue light (and preferably also green light) in the sphere.

This enables the intensity to be more accurately determined than would be the case if the intensity measurement was indirect, for example involving measuring a characteristic of the power e.g. voltage and/or current and/or pulse frequency/duration—depending on how intensity is controlled and inferring the intensity from that measurement, as it takes into account any drift or fluctuations in the efficiency of the source of blue light.

Preferably, the adjustment means is operable to adjust the intensity of the blue LED, preferably by means of a process of pulse frequency modulation.

The intensity could be varied by varying the amplitude of the voltage supplied to the LED or by a process of pulse width modulation of the supplied voltage, but these approaches cause corresponding variations in the wavelength of light emitted by the blue LED. Such variations do not appear to arise if the power supplied to the LED takes the form of a train of a series of equal amplitude pulses, each of equal width, of varying inter-pulse intervals (i.e. having a frequency of occurrence which is modulated to control the intensity).

Preferably, the flicker photometer also includes background illumination means for providing a continuously illuminated background area that surrounds and extends to the perimeter of each stimulus.

The background illumination means can preferably be set so that at the flicker null setting (at which flicker is minimized or eliminated), the stimulus luminance matches that of the surround. This provides the subject with an additional clue as to where the flicker null point is to be found.

Preferably, said background is green, and the background illumination means comprises a second integrating sphere positioned in front of the first integrating sphere and having two apertures through which said area of surface in the first integrating sphere is, in use, viewed.

Preferably, the apparatus includes aperture means between integrating spheres, the aperture means defining the perimeter of each of the two stimuli.

Preferably, the aperture means comprises a small and a large aperture, each corresponding to a respective size of stimulus, and an aperture holder moveable into either selected one of two possible positions, in each of which a respective aperture is visible through the apertures in the second sphere.

The aperture holder may conveniently be rotatable and may be connected to a rotary solenoid for moving the holder into and out of each said position.

Preferably, the front of the holder has a light scattering screen around at least the small aperture so that when the small aperture is selected the background extends to the perimeter of the small stimulus. Preferably there is also a similar screen having a similar purpose, around the large aperture, where the latter is larger than the apertures in the second sphere.

Preferably, the interior of the front hemisphere of the second integrating sphere is black. This helps to prevent the flickering blue and green light from the first spheres being reflected onto the surface or surfaces which provide the background.

Preferably, the apparatus includes a data processor operable to calculate, from the intensity measurements taken using the large and small stimuli, the optical density of the macular pigment of the eye under examination.

To that end, the processor is preferably programmed to calculate an optical density, D, at the wavelength of the light emitted by the blue light source, as the logarithm of the ratio of the measurement obtained using the small stimulus to that obtained using the large stimulus.

Where the blue light source emits light of a wavelength or peak wavelength which is different from 460 nm and, in addition, emits light over a broad band of wavelengths, the processing means may also to advantage be operable to calculate, from D, a value, $D_{460}$, of the optical density of macular pigment in light of a wavelength of 460 nm.

To that end, the processing means may to advantage be programmed to calculate $D_{460}$ using a third order polynomial, preferably the equation:

$$D_{460} = -0.006857 + 1.602D - 0.4726D^2 + 0.9905D^3$$

The numerical coefficients in this equation may need to be tailored to conform with the specific emission spectra of LEDs that are used in the instrument.

Preferably, the processor is also programmed to calculate the lens optical density of said eye using the intensity measurement of blue light obtained with the larger stimulus, and also an intensity measurement of green light with said stimulus.

The latter measurement can be taken using the photodetector that is used to measure the blue light intensity.

In this case, the lens optical density, L425 in light of a wavelength of 425 nm is preferably calculated using a polynomial equation, preferably the equation:

$$L_{425} = -1.6414 + 1.2585\left(\frac{P_B}{P_G}\right) - 0.2009\left(\frac{P_B}{P_G}\right)^2 + 0.0193\left(\frac{P_B}{P_G}\right)^3$$

Where $P_G$ is the measured intensity of green light in the stimulus and $P_B$ is the measured intensity of blue light, when said flickering is minimized or eliminated in the peripheral regions of the stimulus.

The numerical coefficients in this equation may need to be tailored to conform with the specific emission spectra of the LEDs and the spectral sensitivity of the photodetector that are used in the instrument.

This equation does not include the subject's age and the density can therefore be calculated without that particular piece of data. In fact, both $$\left(\frac{P_B}{P_G}\right)$$

and $L_{425}$ are functions of age which can therefore be cancelled out in the derivation of the equation.

According to a second aspect of the invention, there is provided a method of measuring the macular pigment in the eye of a subject, the method comprising the steps of:

(a) presenting to the subject a small flickering stimulus of a rapidly alternating sequence of colors, the stimulus being substantially wholly incident on the macula of said eye;

(b) adjusting the relative intensity of light at least one of said colors until no flickering or minimal flickering is perceived by the subject;

(c) determining the adjusted intensity of said color of light at which this occurs;

(d) before or after the aforesaid steps, presenting to the subject a large flickering stimulus which is incident on both the macula of the subject's eye and a portion of the retina of that eye sufficiently far from the macula to have substantially no macular pigment, the large stimulus being of two alternating colors;

(e) adjusting the intensity of light of one of said colors until said flicker in the large stimulus is minimized or eliminated in the part of the stimulus which is not incident on the macula;

(f) determining said adjusted intensity of light; and (g) mathematically combining the two determined intensities in order to calculate the macular pigment density and eliminate the possible effect on the measurement taken using the small stimulus of the yellowing of the eye under examination.

Preferably, the alternating colors for the stimuli are blue and green, and said intensity adjustment is achieved by adjusting the intensity of the blue light from the stimuli.

According to a third aspect of the invention, there is provided apparatus for use in the measurement of lens optical density of an eye under examination, the apparatus comprising illumination means for illuminating an area with the light of a rapidly repeating sequence of different colors, to provide a stimulus for said eye, viewing elements through which the eye views said stimulus at not less than the minimum distance from the area, the size of the stimulus being such as to encompass, in the eye, both the macula and a portion of the retina having no macular pigment, intensity adjustment means for adjusting the intensity of light of at least one of the colors relative to another of the colors until any flicker in the stimulus as perceived by the eye is minimized or eliminated, and measurement means for determining the intensity of light of said one of the colors at which this occurs.

Preferably, the illumination means is operable to illuminate the area in a rapidly repeating sequence of colors in the form of an alternating sequence of the colors blue and green, the adjustment means preferably being operable to adjust the intensities of light of both colors.

Preferably, the apparatus includes a data processor for calculating the lens optical density in the blue light (preferably of a wavelength of 425 nm) using measured intensities of blue and green light at which said flicker is minimized or eliminated, and preferably for also calculating the equivalent age of the lens.

According to a fourth aspect of the invention, there is provided a method for mathematically compensating for the effect of the lens optical density of an eye under examination on the measured value of the optical density, $D_{460}$, of the macular pigment at a wavelength of 460 nm.

BRIEF DESCRIPTION OF THE DRAWINGS

The invention will now be described, by way of example only, with reference to the accompanying drawings in which:

FIG. 1 is a sectional side view of an embodiment of a flicker photometer in accordance with the invention;

FIG. 2 is a plan view of the photometer;

FIG. 3 is a front elevation of an aperture holder of the photometer;

DETAILED DESCRIPTION OF THE DRAWINGS

Figure 4:
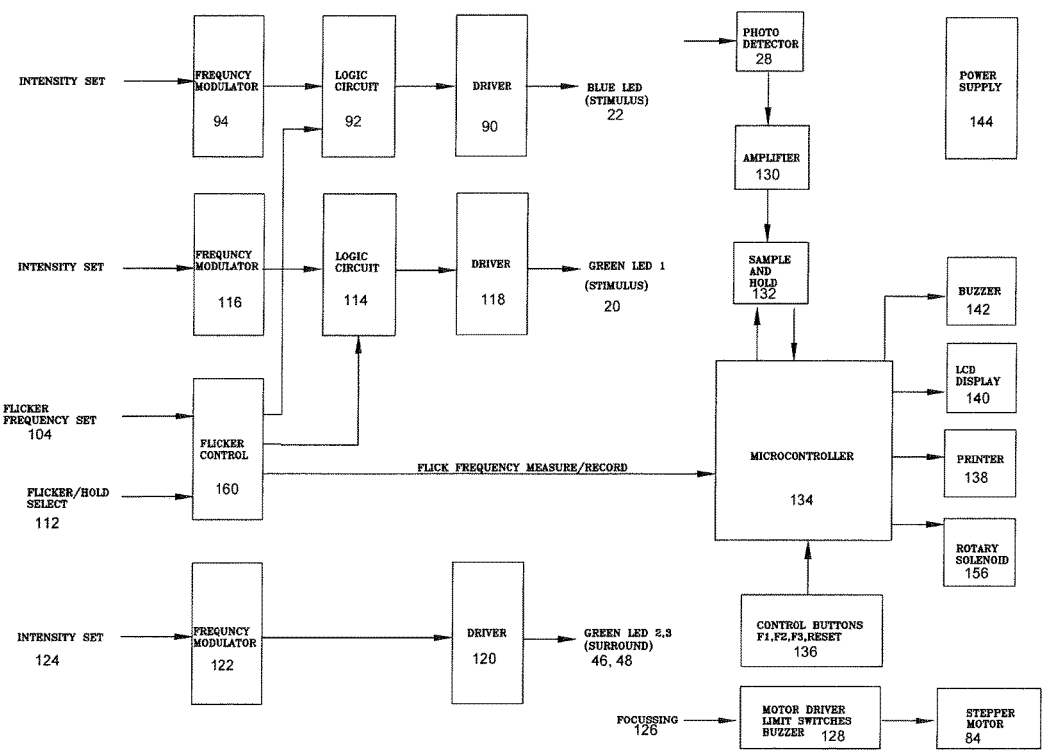
FIG. 4 is a block circuit diagram showing electronic control and measurement circuitry, and a data processor, for the photometer.

With reference to FIGS. 1 and 2, a flicker photometer in accordance with the invention comprises a first integrating sphere 1 and a second integrating sphere 2 which respectively provide diffuse light for a flickering blue and green stimulus and constant green background to be observed by the eye of the subject (not shown) through a telescope comprising an objective condensing lens 4, an aperture 6, an eyepiece lens 8 and an eyepiece viewing aperture 10.

The integrating sphere 1 is constructed from a rear hemispherical portion 12 and front hemispherical portion 14, both of which have radial flanges 16 and 18 at which the two portions are joined together by suitable means (for example by means of a suitable adhesive or some other type of fastener, for example bolts and nuts, acting between the flanges 16 and 18).

The interior surfaces of the two hemispheres 12 and 14 are coated in flat white mat paint which acts as a diffuser for uniformly diffusing light emitted by a one watt green LED 20 and a 3 watt blue LED 22 which are mounted on the top of the front hemisphere 14 and which each extend through a respective hole in the hemisphere 14. Each of the LEDs 20 and 22 is also thermally coupled to a respective heat sink 24 and 26 for dissipating heat generated by the LEDs. The intensity of light emitted by each LED is measured using a photodiode detector 28 mounted in an aperture towards the bottom of the rear hemisphere 12. In use, the flat white inner surface of the integrating sphere 1 acts as a highly efficient scatterer of the light emitted by the sources 20 and 22 so that each source produces a uniform diffuse illumination of the surface, including an area which is diametrically opposed to a circular light outlet opening 30 which is of 32 mm diameter, and is coaxial with the horizontal axis of symmetry of the sphere 1 and with the optical axis of the lenses 4 and 8.

The integrating sphere 1 can be formed from any suitable material, for example a metal or plastics material, and is mounted on a translation slide carriage 32 via a mounting bracket (not shown) which is attached to the carriage 32 and which clamps the two flanges 16 and 18 together.

The integrating sphere 2 is mounted on a carriage 32 in a similar fashion to the integrating sphere 1 and is of a similar construction to the latter, being formed by two hemispheres, each of which has a respective diametric, radial flange 34 and 36 which is attached to flange of the other hemisphere to hold the two parts of the sphere 2 together.

Both spheres have a diameter of approximately 10 cm.

The interior of the rear hemisphere 38 of the sphere 2 is coated with a flat white paint and includes a circular aperture 40 of 28 mm diameter which is coaxial with the aperture 30 in the front hemisphere 14 of the sphere 1. The aperture 40 is diametrically opposed to a 26 mm diameter circular aperture 42 in the front hemisphere 44 of the sphere 2. The front hemisphere 44 also includes two opposed side openings, each of which accommodates a respective one of a pair of one watt green LEDs 46 and 48, each of which is thermally coupled to a (through the respective aperture in the hemisphere 44) respective heat sink 50 and 52 outside the sphere 2.

Mounted on a portion of the carriage 32 between the two spheres is a carrier post 54 the upper end of which supports a rotary solenoid 56 that is connected to a circular aperture holder 58. The holder holds a large aperture 60 and a small aperture 62 which respectively correspond to the large and small stimuli to be provided by the photometer. The apertures 60 and 62 are circular and their centers lie at the same radial position on the circular holder 58. The solenoid 56 is, in use, operable to rotate the holder 58 to bring either of the apertures 60 and 62 into register with the apertures 30 and 40. When either of the apertures 60 and 62 is in such a position, it is coaxial with the apertures 30, 40 and 42, and hence the optical axis of the viewing telescope.

Each of the apertures 60 and 62 is concentric with a shallow, circular, 21 mm diameter recess, which is of larger diameter than either aperture, in the face of the aperture holder 58 adjacent to sphere 1. A 21 mm diameter glass disk is inserted into each recess and is etched with cross-hair markings for the user to view through the viewing telescope.

As can be seen from FIG. 3, the aperture 62, when in register with the aperture 40, will subtend an angle of 1.5° at an eye viewing the aperture through the viewing telescope, whilst the aperture 60 will subtend an angle of 14° at said eye when the aperture is in register with the aperture 40. In use, the light from the sphere 1 when viewed through the apertures 60 or 62 will produce stimuli that subtend corresponding angles.

The front face of the circular holder 58, i.e. the face adjacent the sphere 2 is also provided with a flat white coating so that the area of illumination provided by the LEDs 50 and 52 extends continuously up to the periphery of each aperture in the holder 58 when that aperture is in register with the aperture 40.

A flat black coating (for example from paint) provides a mat black surface on the interior of the hemisphere 44. This surface prevents light that has travelled from the sphere 1 into the sphere 2 from being reflected back onto the flat white surface on the interior of the hemisphere 38, and the front of the aperture holder 58 and the disks therein.

Each of the objective lens 4 and aperture 6 is mounted on a respective carrier 64 and 66 which is in turn mounted on the carriage 32.

The carriage 32 is slideably mounted on a base 68 via a pair of parallel cylindrical rails 70 and 72 attached to the plate 68 through two rectangular vertical end plates 74 and 76. Projecting from the underside of the carriage 32 is a forward rail follower plate 78 which has a pair of spaced circular apertures (not shown) through each of which a respective one of the rails 70 and 72 passes. A similarly apertured rear rail follower plate 80 also extends from the underside of the carriage 32 towards the rear of the latter. The plate 80 also includes a lead screw nut which engages a screw shaft 82 that can be rotated in a controlled manner by a lead screw stepper motor 84. It will be appreciated that the motor 84, shaft 82 and screw nut provide a worm drive by virtue of which operation of the motor 84 will cause the carriage, and the components that it carries, to slide back and forth along the plate 68 in the direction of the optical axis of the telescope.

As can be seen from FIG. 1, the viewing aperture 10 and eyepiece lens 8 are provided on a carrier plate 86 which is itself directly mounted on the plate 68. Consequently, the aperture 10 and eyepiece lens 8 do not move with the carriage. The same carrier also supports a forehead rest 88. The carriage 32 enables the user to adjust the focus of the telescope, constituted by the elements 4, 6 and 8, without having to reposition his or her head, which can remain pressed against the forehead rest 88.

The stepper motor 84, all the LEDs (20, 22, 46, 48), the rotary solenoid 56 and the photodiode 28 are all connected to the circuitry shown in FIG. 4. For the sake of clarity, the circuitry of FIG. 4 and its connections to those components has not been included in FIGS. 1 and 2. The circuitry of FIG. 4 is also connected to various user operable controls (not shown) through which the photometer can be set up and operated.

Figure 5:
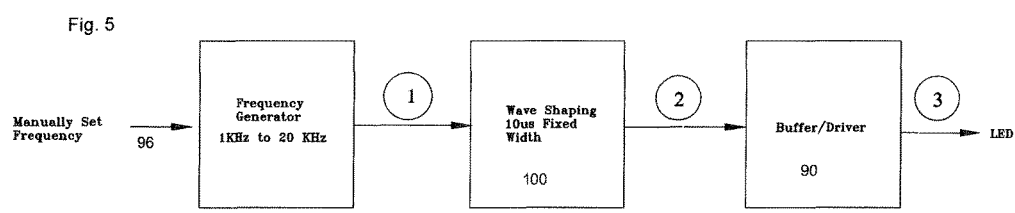
FIG. 5 is a block diagram showing part of the circuitry shown in FIG. 4, for controlling the intensity of light emitted by one of the sources used in the photometer.
Figure 6:
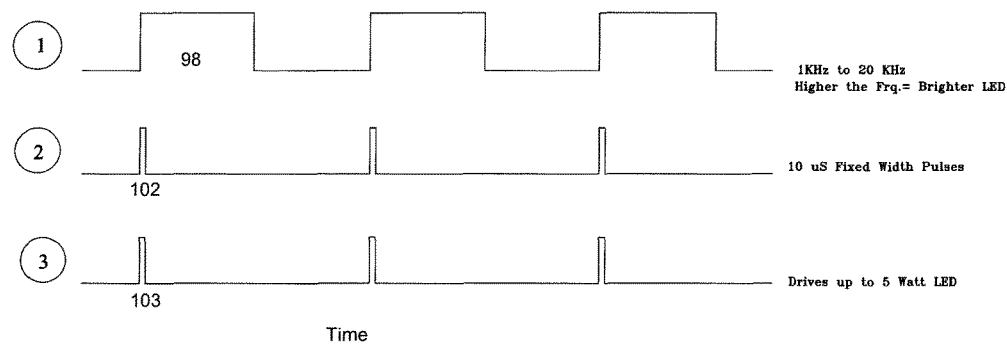
FIG. 6 illustrates the output of the stages shown in FIG. 5.

With reference to FIG. 4, the blue LED 22 of the integrating sphere 14 is supplied with the necessary electrical power to operate it by a driver 90 which is controlled by logic circuit 92 to cause the LED to flicker at a frequency of 10 Hz-40 Hz and at an intensity governed by a frequency modulator 94 which provides one of the input signals for the logic circuit 92. The operation of the frequency modulator is illustrated in FIGS. 5 and 6. The modulator has an input 96 via which the user or clinician can manually set a pulse frequency corresponding to a desired intensity of illumination by the blue LED. A frequency generator generates a square wave signal 98 at the chosen frequency, which is in the range of 1 kHz-30 kHz. This signal is supplied to wave shaping circuitry 100 in the modulator 94. This circuitry converts the square wave signal 98 into a train of pulses, such as the pulse 102, each of which is of a duration of 10 micro seconds. The interval between successive pulses corresponds to the period of the square wave signal 98. Consequently, the frequency of the signal 98 will correspond to the frequency of occurrence of pulses such as the pulse 102 (i.e. the number of such pulses that occur per unit time). These pulses are, in turn, fed to the driver 90 that provides an output in the form of a driving signal for the LED constituted by said pulses. The intensity of light emitted by the LED will be roughly proportional to the frequency of the occurrence of the pulses.

FIG. 5 shows the circuitry 100 connected directly to the buffer 90. In fact, the connection between the circuitry 100 and driver 90 is made via the logic setter 92. That circuit has been omitted from FIG. 5 for the sake of clarity.

The logic circuit 92 has another input that is connected to flicker control circuitry 160. This will feed a square wave signal on the frequency of 10 Hz-40 Hz, determined by a flicker frequency set input 104 to the control circuitry 160. The logic circuit 92 acts as an AND gate which is opened each time that the square wave signals from the circuitry 160 is at a maximum value to allow the train of pulses generated by circuitry 100 to drive the LED 22.

The output of the driver 90 is shown at 103 in FIG. 6, and corresponds to the train of pulses output by the circuitry 100.

Figure 7:
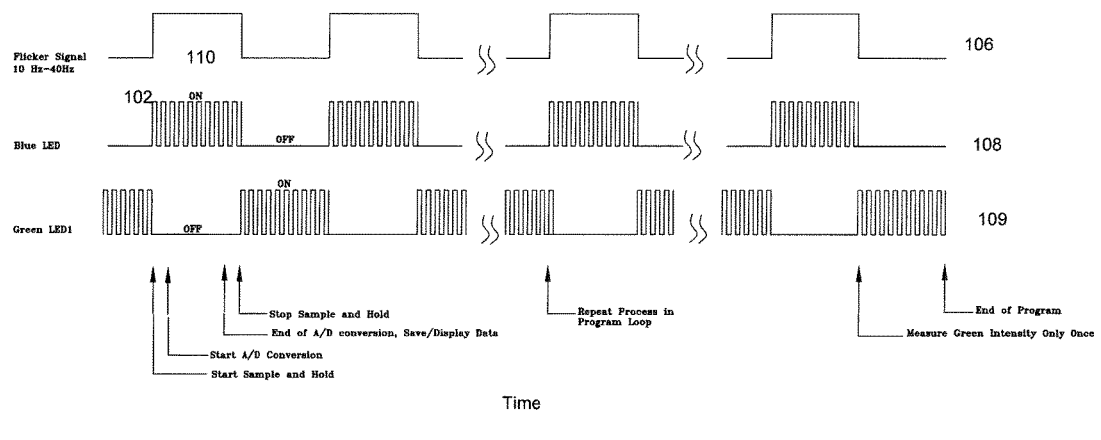
FIG. 7 illustrates the timing sequence of the operation of a photodetector used in the photometer to measure intensity of light produced by two of the photometer's light sources.

In FIG. 7, the square wave 106 represents the signal that is fed by the circuitry 160 to the circuitry 92, whilst the graph 108 represents the signal that is subsequently fed from the logic circuit 92 to the driver 90 (which outputs are corresponding driving voltage/current to the LED 22). As can be seen, during each maximum of the wave form 106, the LED 22 is supplied with a burst of equal amplitude, equal duration pulses such as the pulse 102. Those pulses are not shown to scale in FIG. 108 since in reality there will be, for example, between 50-1000 individual pulses for each "on" part of the square wave cycle 106, for example the portion 110, depending upon the selected intensity, for a flicker of 10 Hz. The frequency of occurrence of the individual pulses is so high that those pulses cannot be individually perceived by the eye and their frequency of occurrence can therefore be controlled to control the perceived intensity of light emitted by the LED 22. However, the signal 106, which corresponds to the frequency of flicker of the LED 22 can of course potentially be perceived by the eye under examination.

Referring back to FIG. 5, the flicker control circuitry 160 supplies a further square wave signal, in antiphase to the signal 106, to a logic circuit 114 which is connected between a frequency modulator 116 and a driver 118 for driving the green LED 20.

The components 116, 114 and 118 respectively correspond to the frequency modulator 94, the logic circuit 92 and driver 90 and thus control the on-off operation and intensity of the LED 20 in a similar fashion to the way in which the LED 22 is controlled. However, since the square wave signals supplied by the circuitry 160 to the logic circuits 92 and 114 are in antiphase the green LED will be switched on when the blue LED is off and vice-versa.

The flicker control circuitry 160 is also connected to a flicker/hold select switch which in one position switches off the flicker of the LEDs 20 and 22 so that both LEDs remain on continuously. When the circuitry 160 is operating in this mode, a constant "on" signal is supplied to both of the logic circuits 92 and 114.

The green LEDs 46 and 48 in the integrating sphere 2 are driven by a common driver 120 which is functionally similar to the drivers 90 and 118, and which is controlled by a frequency modulator 122 which is functionally similar to the frequency modulators 94 and 116, and thus enables the intensity of light emitted by the LEDs 46 and 48 to be controlled, in response to inputs from a control switch or knob 124, by a method of pulse frequency modulation.

In FIG. 7, the graph 109 represents the driving signal sent to the green LED 20.

The controls for the flicker photometer also include a focusing control 126 that controls the operation of the stepper motor 84 (and hence the position of the carriage 32) through control circuitry 128 that includes a motored driver circuit, limit switches for switching off the motor when the carriage is near the end of its permitted range of movement and a warning buzzer which is activated by the closing of either of the limit switches, to provide an audio warning that the carriage 32 has reached either end of its allowable range of movement.

The photodetector 28 is connected at its output to an amplifier 130 which is in turn connected to sample and hold circuitry 132 that includes an analogue to digital converter digitizing the signal detected by the photodetector. The sample and hold circuitry is controlled by a data processor which takes the form of a microcontroller 134. The microcontroller 134 receives a square wave signal from the flicker control circuitry 160 which corresponds to the square wave 106, and uses this to trigger the sample and hold circuitry 132 to sample the output of the photodetector in synchronism with the operation of the LEDs 20 and 22. More specifically, an example of the way in which the sample and hold circuitry 132 is controlled is shown at the bottom of FIG. 7. As can be seen, successive analogue to digital conversion and sample and hold operations are conducted when the blue LED is active, whereas the intensity of the green LED is measured only once (on start-up of the photometer or each time the intensity set input of the frequency modulator 116 is adjusted). The microcontroller 134 has further inputs which are connected to control buttons F1, F2, F3 and reset, represented by block 136, the functions of which are discussed below.

Microcontroller 134 also has an output for controlling the rotary solenoid 56 for supplying data to a printer 138 and a signal to an LCD display 140.

The microcontroller 134 may also be programmed to activate a buzzer 142 if certain predetermined conditions arise. The path operating the various components of the circuitry shown in FIG. 4 is provided by a power supply 144 which, for the sake of clarity, is shown with its connections to the various other components omitted.

Figure 9:
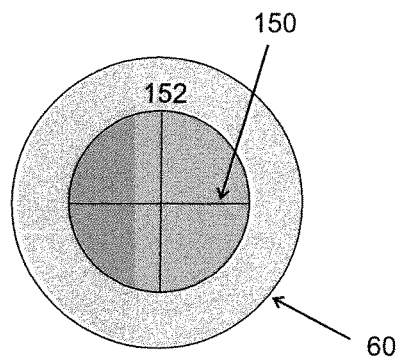
FIG. 9 is a corresponding view in the situation in which the photometer provides a large stimulus.
Figure 8:
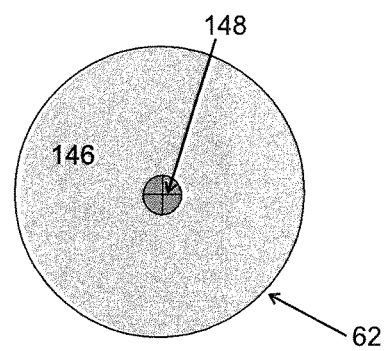
FIG. 8 illustrates the image seen by a subject when the photometer provides a small stimulus for the subject's eye.

The microcontroller 134 is programmed to calculate lens optical density equivalent age of lens and macular pigment density of an eye under examination in the way discussed below, by means of intensity measurements (via the photodetector 28) made during the course of the observation of the flickering stimuli shown in FIGS. 8 and 9, as seen through a telescope. FIG. 8 shows the small stimulus which is, in effect, the alternating blue and green light from the integrating sphere 1 which is viewed through the aperture 62. The sphere 2 and the front face of the holder 58 provide a continuous green background light which is in the shape of a ring 146 concentric with the aperture 62. The cross hairs etched onto the glass substrate of the aperture 62 are shown at 148. FIG. 9 shows the situation after the solenoid 56 has moved the larger aperture 60 into register with the aperture 40 to provide a larger circular stimulus. The cross hairs for this stimulus are shown at 150 and again, the flickering stimulus is visible against a continuous green annular background, here referenced 152, provided via the interior of the hemisphere 38 of the sphere 2.

Figure 10:
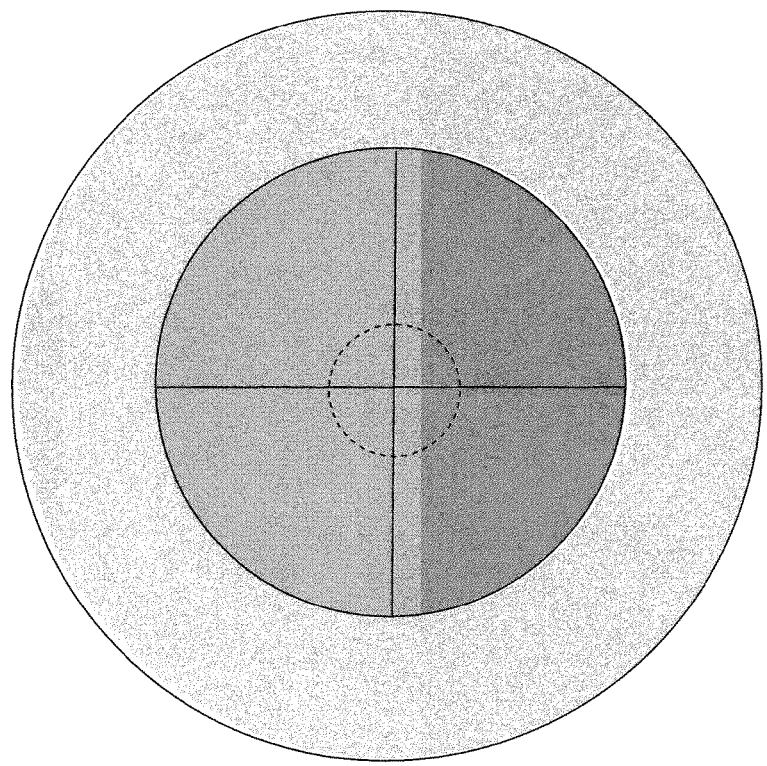
FIG. 10 is a corresponding view showing the large stimulus and illustrating the region of that stimulus which would be incident on, and thus seen via, the macula of the subject.

After the photometer has been initially set up by selecting the intensity of the continuous green background and the light emitted by the LED, as well as the flicker frequency for the LEDs 20 and 22, as discussed below, the subject will attempt to adjust the intensity of light emitted by the blue LED 20 until, in the case of the image presented in FIG. 8, the central stimulus seen through the aperture 62 no longer appears to flicker. The subject or operator then presses a button, F2, which is an input to the microcontroller 134 to trigger the recordation of the intensity of blue light at which this occurs. Additionally, the action of pressing button F2 causes the blue light intensity setting to be given a small disturbance via the microcontroller 134 prior to the subject attempting a subsequent setting. When the subject is looking at the larger flickering stimulus, as shown in FIG. 9, the object is to keep looking at the center of the cross hairs 150 and adjust the intensity of light emitted by the blue LED until the entire stimulus seen through the aperture 60 (apart from that in the very center) has stopped flickering. The subject or operator then presses the button F2 to record the intensity of light emitted by the LED 20 once this occurs, and this data can be used either in the calculation of the lens optical density or equivalent age of lens or to take the lens optical density into account in the calculation of macular pigment density. FIG. 10 shows, within the dotted line 154, the central region in which flicker will be retained.

On the system block diagram of FIG. 4, "flicker frequency set" which refers to the frequency of the flicker signal, needs to be adjustable by the operator. For example, the frequency can initially be set to default values of 25 and 32 Hz for the 1.5° and 14° stimuli, respectively. Sometimes, there may be slight frequency adjustments to suit the individual subject. For example with the 1.5° stimulus, if the frequency is too high for the subject, flicker will be eliminated over a wide range of blue LED intensity settings, and if the frequency is too low, flicker can never be eliminated.

The flicker/hold select switch 112 is a 2-position switch. In one position (hold), the flicker is switched off and both the blue and green LEDs in the left-hand sphere that form the stimulus are turned on, rather than alternating. In the other position (flicker), the LEDs alternate. The switch is placed in the hold position during initial setup of the device (see below), and also while the subject is adjusting the focus. It is a little easier to do this with a steady stimulus rather than one that is flickering. Switching off the flicker is also an automatic function performed by the microcontroller at the start of a measurement session, since it is at this time that the subject needs to adjust the focus. The control buttons F1, F2 and F3 are explained below.

Flicker frequency is not measured by the photodiode but rather it is inferred from the frequency fed to the blue and green LEDs. Specifically, the block 160 is a frequency generator whose frequency is adjustable by the operator. Note that the outputs (square wave signals) control the logic circuits for the blue and green LEDs that form the stimulus. The logic circuits permit the high frequency pulses generated by the two frequency modulators to be fed alternately to the respective LED drivers, thus achieving flicker. The frequency generator output is also fed to the microcontroller 134 which in turn measures the frequency. The photodetector 28 is continuously measuring the light intensity inside the sphere 1. However, the microcontroller 134 can now indicate to the sample and hold block when to sample the amplified photodetector signal and send it to the microcontroller 134. During a test, when the subject is adjusting the blue LED 22 intensity, sampling is performed during the phases of the cycle when the blue LED is on. At the end of the test, a single sample is obtained during the phase when the green LED is on. This latter measurement is needed for the lens optical density calculation.

Operation of Photometer

In the initial, one-time set-up, the green surround luminance (sphere 2) is adjusted to a value of ~20 candelas/m$^2$, as measured with a Minolta Spotmeter. With the flicker/hold switch in the hold position, and with the blue LED in the sphere 1 turned off, the green LED in that sphere is adjusted in intensity until the stimulus luminance matches that of the surround. Since the green color appearance of stimulus and surround are identical, this luminance matching can be easily accomplished by eye, in fact more accurately than by using the Spotmeter. The luminance value of 20 candelas/m$^2$ is chosen with two criteria in mind. Firstly, the luminance level should be comfortable with no high intensity glare problems. Secondly, during the test, subjects with macular pigment optical densities (MPOD) ranging from zero to over 1.0 have to be accommodated, i.e. able to match the luminances of the blue and green components of the stimulus (as judged by absence of flicker). If the green LED intensity is set too high, then subjects with high MPOD will not be able to increase the blue LED intensity sufficiently to achieve a match. Likewise, if it is set too low, then subjects with very low MPOD will not be able to decrease the blue LED intensity sufficiently to achieve a match. (Note that the lowest blue LED intensity setting is not zero.)

The procedure for testing a subject is as follows: When the instrument is switched on, the 1.5° stimulus aperture is automatically positioned in the field of view. The microcontroller automatically switches off the flicker and the subject is asked to press either of two focusing buttons, which cause the translation carriage to move backwards or forwards, until the stimulus is seen in sharp focus. A screen displays the frequency so that the operator can set the flicker frequency at 25 Hz and then press the F1 control button. The screen now displays the blue LED intensity and the stimulus automatically begins to flicker. The subject adjusts this intensity via a control knob to minimize flicker. The operator presses the F2 control button to record the setting and then to provide an automatic offset to the setting. This is repeated as many times as required (usually 5 times). If, during the test, the subject requires an adjustment to the frequency, the operator presses the F3 control button and the frequency is displayed on the screen. After adjusting the frequency, the operator presses F3 again and the test is resumed. When enough settings have been recorded, the operator presses the F1 button. This causes the rotary solenoid to be energized and the 14° stimulus appears in the field of view. The screen displays the frequency which is set by the operator at 32 Hz after which F1 is pressed and the screen again displays the blue LED intensity. The test proceeds as with the 1.5° stimulus except that the subject adjusts the blue LED intensity to achieve the situation where flicker is only perceived at the center of the stimulus. When sufficient settings have been recorded (again typically 5), the operator presses F1, and the screen displays the MPOD and the standard error in MPOD, together with the lens optical density and associated standard error and the equivalent age of the lens. This information is transmitted to a printer. Upon pressing the reset button, the instrument is initialized for the next subject or for a repeat test with the same subject.

The lens optical density measurement requires only the measurement with the large stimulus where the setting made by the subject (steady appearance in the peripheral part of the stimulus) is independent of macular pigment.

A control knob, which provides the 'intensity set' input from the modulator, allows the subject to alter the intensity of the blue component of the stimulus. For the 1.5° stimulus, this intensity adjustment is made to minimize, or eliminate, the flicker seen in the stimulus, and this occurs when the blue and green components are equalized in terms of luminance. The wavelengths of the two colors, blue and green, are chosen to correspond to maximum absorption (blue) and zero, or close to zero, absorption (green) by the macular pigment. Subjects having a high macular pigment density will need to increase the blue intensity to compensate for attenuation by the macular pigment (which lies in front of the retinal photoreceptors). Likewise subjects with a low density of macular pigment will need to lower the intensity. However, other factors, particularly yellowing of the lens which increases with age, will affect the subject's intensity setting. To remove such effects, the subject repeats the test using the 14° stimulus, also viewed centrally. The subject adjusts the intensity of the blue component to the point where flicker is eliminated over most of the stimulus with the exception of a small, residual flicker at the center. (Increasing or decreasing the blue intensity from this setting causes the entire stimulus to flicker.) The steady appearance in the peripheral region of the stimulus, where macular pigment has negligible influence, means that the blue and green luminances have been matched in the peripheral retina. Subjects with a lot of lens yellowing will require a higher blue intensity than those with less lens yellowing.

The luminance of the green component of the flickering stimulus is pre-set to be equal to that of the green surround. Thus at the flicker null point, the luminance of the stimulus matches that of the surround. This provides the subject with an additional clue in searching for the flicker null point. If the stimulus is flickering but appears brighter than the surround, the subject must reduce the intensity of the blue component of the stimulus. If the stimulus is flickering but appears darker than the surround, the subject must increase the intensity of the blue component of the stimulus.

From the ratio of blue intensity settings obtained with the two stimuli, the effect of lens yellowing is eliminated, and the macular pigment optical density, D, can be calculated:

$$D = \log_{10} \frac{I_{Small\ stimulus}}{I_{Large\ stimulus}} \quad (1)$$

The ratio of intensities of the blue and green components obtained with the 14° stimulus provides an index, LY, of the degree of lens yellowing:

$$LY = \frac{I_{Blue}}{I_{Green}} \quad (2)$$

The blue LED has a peak wavelength of ~455 nm, close to that of the macular pigment's peak absorption wavelength. The green LED has a peak wavelength of ~520 nm where macular pigment absorbance is very small. However, the LEDs have relatively wide bandwidths, and a correction has to be made to the macular pigment optical density calculated from equation (1) in order to be able to report the peak value at 460 nm, $D_{460}$. This quantity is found by solving numerically the equation:

$$D = \log_{10}\left\{\frac{\int E_G(\lambda)10^{-D_{460}\cdot\varepsilon(\lambda)}V(\lambda)d\lambda}{\int E_B(\lambda)10^{-D_{460}\cdot\varepsilon(\lambda)}V(\lambda)d\lambda} \cdot \frac{\int E_B(\lambda)V(\lambda)d\lambda}{\int E_G(\lambda)V(\lambda)d\lambda}\right\}$$

where $E_G(\lambda)$ and $E_B(\lambda)$ are the energy spectra of the green and blue LEDS, $V(\lambda)$ is the 10° photopic luminosity function, and $\varepsilon(\lambda)$ is the normalized extinction spectrum of macular pigment. The microcontroller is pre-programmed to perform the calculations and the results are displayed on a screen.

The LEDs are fed with high frequency pulses of fixed voltage whose frequency is adjustable. The effect is a change in the perceived brightness. (The frequency is much greater than the flicker fusion frequency of the human eye.) Alternative methods, such as simply altering the LED voltage or using pulse-width modulation, were found to produce small wavelength shifts in the peak LED wavelengths. The LEDs are mounted on heat sinks without which the light intensity was found to drift.

Square wave alternation between the blue and green LEDs to produce flicker is achieved electronically. The LED intensity is measured via a photodiode detector mounted inside the sphere 1. Electronic gating is used to ensure that the photodiode samples the light inside the sphere only when the blue LED is on, or only when the green LED is on.

The instrument is provided with a low power telescope. All of the components except the eye-piece lens are mounted on a translation slide so that they can be moved relative to the eyepiece lens in order to be able to accommodate both myopic and hyperopic subjects. The objective lens produces a real image of the 1.5 or 14° apertures, which are provided with cross-hairs to facilitate central fixation, in the plane of the field stop 6. The subject adjusts the position of the translation slide until the entire field of view is sharply focused.

The spacing between the integrating spheres 1 and 2 and the sizes of the openings are optimized to reduce cross-over of light from one sphere to the other. To further reduce this problem, the front half (closer to the telescope) of the right-hand sphere 2 is coated on the interior surface with a very low reflectance, flat black paint. The other interior surfaces are painted with a flat white paint.

Numerical Solution of Equation $$D = \log_{10}\left\{\frac{\int E_G(\lambda)10^{-D_{460}\cdot\varepsilon(\lambda)}V(\lambda)d\lambda}{\int E_B(\lambda)10^{-D_{460}\cdot\varepsilon(\lambda)}V(\lambda)d\lambda} \cdot \frac{\int E_B(\lambda)V(\lambda)d\lambda}{\int E_G(\lambda)V(\lambda)d\lambda}\right\} \quad (1)$$

where $E_G(\lambda)$ and $E_B(\lambda)$ are the energy spectra of the green and blue LEDS, $V(\lambda)$ is the 10° photopic luminosity function, and $\varepsilon(\lambda)$ is the extinction spectrum of macular pigment, normalized to unity at its peak value which occurs at a wavelength of 460 nm.

D is obtained from the blue LED intensity measurements:

$$D = \log_{10}\frac{I_{Small\ stimulus}}{I_{Large\ stimulus}}$$

The required quantity is the peak macular pigment optical density, $D_{460}$.

To solve equation (1) numerically, we first approximate the integrals by finite sums:

$$D = \log_{10}\left\{\frac{\sum E_G(\lambda)10^{-D_{460}\cdot\varepsilon(\lambda)}V(\lambda)\Delta\lambda}{\sum E_B(\lambda)10^{-D_{460}\cdot\varepsilon(\lambda)}V(\lambda)\Delta\lambda} \cdot \frac{\sum E_B(\lambda)V(\lambda)\Delta\lambda}{\sum E_G(\lambda)V(\lambda)\Delta\lambda}\right\} \quad (2)$$

where the interval, $\Delta\lambda$, was chosen to be 5 nm. The sums are carried out over the wavelength range 400 to 600 nm since $E_G(\lambda)$ and $E_B(\lambda)$ are zero outside that range. The following algorithm is then implemented:
1. Set $D_{460}$ to zero
2. Using known values (at 5 nm intervals) of the wavelength-dependent quantities in equation (2), calculate D
3. Record D and $D_{460}$
4. Increase $D_{460}$ by 0.01
5. If $D_{460}$ is greater than 1.5, stop, otherwise—
6. Go to statement 2

Figure 11:
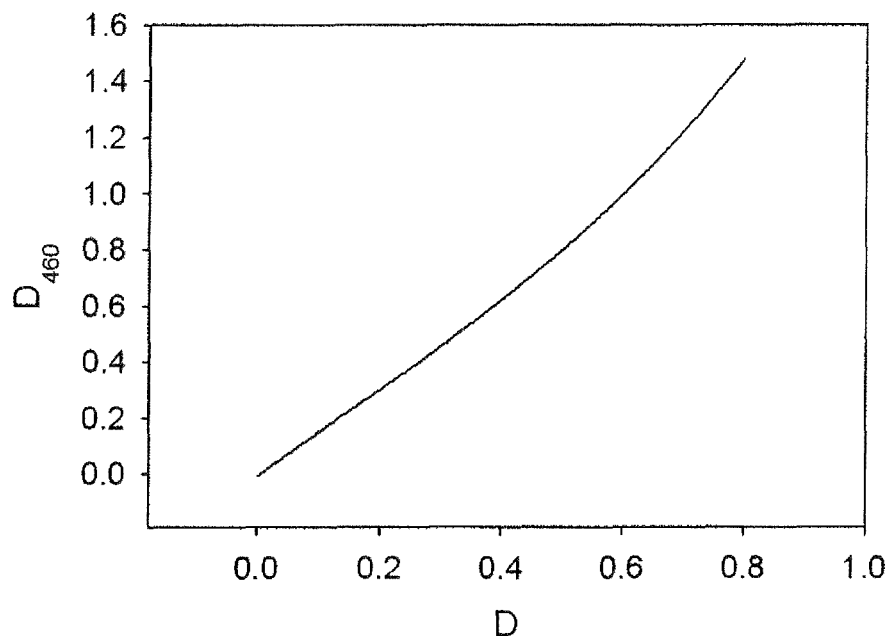
FIG. 11 is a graph of data used in deriving the method of calculating macular pigment optical density from measurements obtained using the photometer.

From the recorded values of D and $D_{460}$, a graph of $D_{460}$ as a function of D is generated covering the range $0 \leq D_{460} \leq 1.5$. (Subjects with values of $D_{460}$ outside this range have never been encountered), and this is shown in FIG. 11.

To facilitate the use of this graph, a polynomial is fitted to the data. (A third order cubic was found to be adequate). Using energy spectra obtained from typical blue and green LEDs, the following polynomial was generated:

$$D_{460} = -0.006857 + 1.602D - 0.4726D^2 + 0.9905D^3$$

The instrument microprocessor is programmed with this equation so that a value of $D_{460}$ may be generated automatically from the subject's blue LED intensity settings. Additionally, the microprocessor is programmed to allow the subject to make a number (typically 5 to 10) of settings with both the 1.5° and 14° stimuli, and to calculate the mean value of $D_{460}$ and the associated standard error Calculation of Lens Optical Density at 425 nm The lens optical density at a wavelength of 425 nm, $L_{425}$, is determined from the subject's instrument settings made with the 14° stimulus. When the subject has determined the null point (residual flicker in the middle of the visual field only), let the photodiode detector readings for the blue and green components of the stimulus be $P_B$ and $P_G$ respectively.

We first calculate the 10° photopic luminosity function, $V(\lambda)$, as a function of age using a published algorithm (Sagawa, K and Takahashi, Y (2001) Spectral luminous efficiency as a function of age. J. Opt. Soc. Am. 18, 2659-2667):

$$\log_{10}V(\lambda) = \log_{10}V_{64.9}(\lambda) + (a-64.9)\log \Delta V(\lambda)$$

where a is age in years and $V_{64.9}(\lambda)$ is the 10° photopic luminosity function for a person aged 64.9 years.

We then calculate the theoretical ratio, $P_B/P_G$ as a function of age by numerically solving the equation:

$$P_B/P_G = \frac{\int E_G(\lambda)V(\lambda)d\lambda}{\int E_B(\lambda)V(\lambda)d\lambda} \cdot \frac{\int E_B(\lambda)PD(\lambda)d\lambda}{\int E_G(\lambda)PD(\lambda)d\lambda}$$

where $PD(\lambda)$ is the spectral sensitivity of the photodiode detector. To do this, the integrals are replaced by sums (over the wavelength range 400 to 600 nm) and $d\lambda$ is replaced by $\Delta\lambda$ with a value of 5 nm. Thus:

$$P_B/P_G = \frac{\sum E_G(\lambda)V(\lambda)\Delta\lambda}{\sum E_B(\lambda)V(\lambda)\Delta\lambda} \cdot \frac{\sum E_B(\lambda)PD(\lambda)\Delta\lambda}{\sum E_G(\lambda)PD(\lambda)\Delta\lambda}$$

The lens density at 425 nm, $L_{425}$ as a function of age is obtained from:

$$L_{425} = 1.0062 + (a-64.9)0.0143$$

where the figure 1.0062 is the value of $L_{425}$ for a 64.9 year old and the figure 0.0143 is the decrease per year in $\log_{10}V$ at 425 nm (assumed to be due to increased lens optical density).

Figure 12:
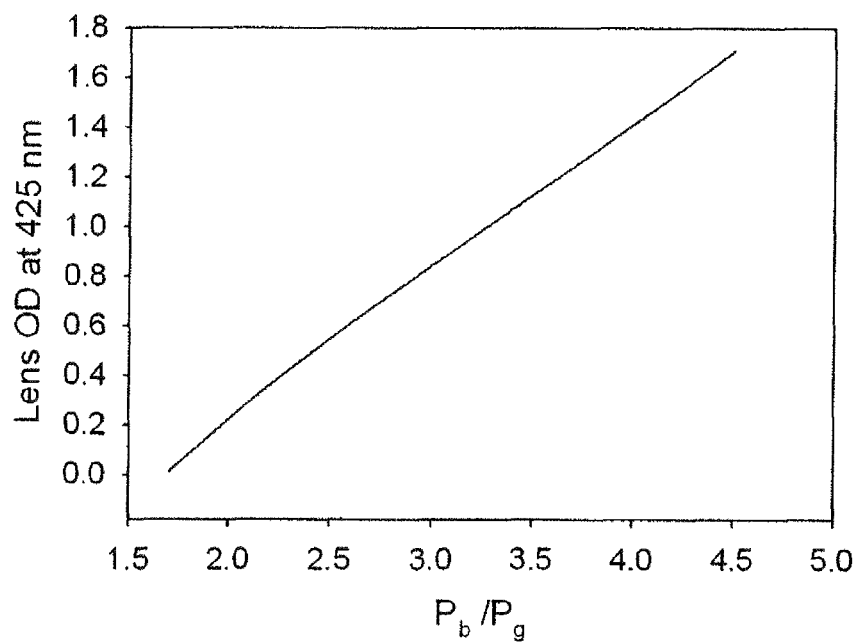
FIG. 12 is a graph of data used in deriving the method of calculating lens optical density from such measurements.

Since we now have both $L_{425}$ and $P_B/P_G$ as functions of age, we can prepare a graph of $L_{425}$ as a function of $P_B/P_G$, as shown in FIG. 12.

To facilitate the use of this graph, a polynomial is fitted to the data. (A third order cubic was found to be adequate). Using energy spectra obtained from typical blue and green LEDs, and the spectral sensitivity of the photodiode detector, the following polynomial was generated:

$$L_{425} = -1.6414 + 1.2585\left(\frac{P_B}{P_G}\right) - 0.2009\left(\frac{P_B}{P_G}\right)^2 + 0.0193\left(\frac{P_B}{P_G}\right)^3$$

The instrument microprocessor is programmed with this equation so that a value of $L_{425}$ may be generated automatically from the subject's value of $P_B/P_G$. Additionally, the microprocessor is programmed to allow the subject to make a number (typically 5 to 10) of settings with the 14° stimuli, and to calculate the mean value of $L_{425}$ and the associated standard error. Substituting the value of $L_{425}$ obtained for a subject into equation 3, we can calculate the equivalent age, a, of the subject's lens. This step is also programmed into the microcontroller.

Correcting the Macular Pigment Optical Density Measurement for Lens Density Effects In order to obtain a more accurate value of the peak macular pigment optical density, $D_{460}$, the 10° photopic luminosity function, $V(\lambda)$, in equations (1) and (2) must be adjusted based upon the equivalent age of the subject's lens. As shown above, $V(\lambda)$ at any age can be calculated using the published algorithm of Sagawa and Takahashi (J. Opt. Soc. Am. 18, 2659-2667). Accordingly, $D_{460}$ would be calculated from equation (2) once the lens equivalent age has been calculated. The instrument microprocessor is programmed so that a corrected value of $D_{460}$ may be automatically generated.

A Means of Improving the Accuracy of Measurements Made with the Mapcat

Photometer intensity measurements may be adversely affected by the presence of unwanted stray light which would have the effect of making the LED intensity measurements higher than would be the case with no stray light. Potential sources of stray light are ambient room light penetrating the instrument case, for example through the cooling fan exhaust vent, and light from the green LEDs in sphere 2. To eliminate the effects of stray light, improvements have been made to the microprocessor code. When the instrument is switched on, the microprocessor code provides an instruction to turn off the power to the blue and green LEDs in sphere 1 (but not the green LEDs in sphere 2) by means of a transistor switch. Next there is a second instruction to sample the stray light intensity in sphere 1 with the photodiode detector, and to record the value, $I_{stray}$. Thereafter, the test measurements proceed as previously described with the following provision: From each blue and green LED intensity measurement made during subject testing, $I_{stray}$ is subtracted. The advantage of this procedure is that the instrument will provide accurate measurements that are independent of the ambient lighting in the testing location.

A Means of Automatically Calibrating the Photodiode Detector

The intensities of the blue and green LEDs in sphere 1 are measured with photodiode 28 mounted in a port in integrating sphere 1. A one-time calibration of the photodiode is necessary for accurate intensity measurements. An additional port is introduced in sphere 1 into which a calibrated photodiode can be temporarily inserted. A two-way switch connects either the photodiode 28 or the calibrated photodiode to the detector circuitry. The calibration proceeds as follows: The blue LED is switched on and its intensity is adjusted to a value that is approximately the average of the values to be expected during subject testing. The intensity measured by photodiode 28 is recorded, $I_{B,28}$, as well as the intensity recorded by the calibrated photodiode, $I_{B,CAL}$. The blue LED is switched off and the green LED is switched on. The intensity measured by the photodiode is recorded, $I_{G,28}$, as well as the intensity recorded by the calibrated photodiode, $I_{G,CAL}$. A calibration factor, F, is calculated as $$F = \frac{I_{B,28} I_{G,CAL}}{I_{G,28} I_{B,CAL}}$$

A line is introduced into the microprocessor code following the line pertaining to the acquisition of a green LED intensity measurement, $I_G$:

$$I_G = I_G \times F$$

i.e. an instruction to multiply the measured intensity $I_G$ by the factor F and store this as the corrected value.

After this calibration procedure, the calibrated photodiode is removed from the port in sphere 1 and replaced by a plug whose inner surface is coated with the same flat white paint used to coat the interior of the sphere.

The calibration procedure can be automated by appropriate programming of the microprocessor and electronic switching that will allow either photodiode 28 or the calibrated photodiode to be selected. After inserting the calibrated photodiode in sphere 1, a dedicated button is depressed, initiating the sequence of steps described above including calculation of the factor, F, and the subsequent modification of $I_G$.

What is claimed is:

1. An apparatus for use in the measurement of macular pigment optical density in an eye under examination, the apparatus comprising illumination means wherein the illuminating means comprises a blue light source and a green light source which alternately illuminate an area constituted by a light diffusing surface wherein the light diffusing surface comprises an integrating sphere for illuminating an area with light, to provide a stimulus for said eye wherein the apparatus includes a photodetector for measuring the intensity of light in the sphere; intensity adjustment means for adjusting the intensity of light of one of the colors relative to light of another of the colors, until any flicker in the stimulus perceived by the eye is minimized or removed; measurement means for determining the intensity of light of said one of the colors at which said minimizing or removal of flicker occurs; wherein the apparatus includes size selection means for enabling the size of the stimulus to be selected from either a small size, in which all or most of the stimulus falls on the macula of the eye, or a large size, in which the stimulus extends to a portion of the retina of the eye at which there is substantially no macular pigment; and calibration means wherein the calibration means comprises adjusting the intensity using a calibrated photodiode prior to measurement of macular pigment optical density.

2. The apparatus of claim 1, wherein the apparatus includes viewing elements via which, in use, either stimulus is viewed by the eye under examination at a set minimum distance from the illuminated area that provides the stimuli, so that the angle that each stimulus subtends at the eye is controlled or constrained and further wherein the small stimulus subtends an angle of not more than 1.5° at the eye under examination and wherein at least part of the large stimulus subtends an angle of at least 14° at the eye under examination.

3. The apparatus of claim 2, wherein the viewing elements comprise a telescope.

4. The apparatus of claim 2, wherein the light sources comprise a blue LED and a green LED wherein the adjustment means is operable to adjust the intensity of the blue LED and wherein the power supplied to the LED takes the form of a train of a series of equal amplitude pulses, each of equal width and of varying inter-pulse-intervals.

5. The apparatus of claim 2, wherein the blue light source emits light of a wavelength or peak wavelength which is different from 460 nm, the processor means being operable to calculate a value, $D_{460}$, of the optical density of macular pigment in light of a wavelength of 460 nm from the measured optical density D obtained using blue light and the wavelength of light emitted by the blue light source.

6. The apparatus of claim 5, wherein the processor is programmed to calculate $D_{460}$ using the equation:
$D_{460} = -0.006857 + 1.602D - 0.4726D^2 + 0.9905D^3$ and further wherein the numerical coefficients are adjusted to be consistent with the spectral properties of the specific blue and green LEDs used in the apparatus.

7. The apparatus of claim 6, wherein the lens optical density, $L_{425}$, to light of wavelength 425 nm is calculated by means of the following equation:

$$L_{425} = -1.6414 + 1.2585\left(\frac{P_B}{P_G}\right) - 0.2009\left(\frac{P_B}{P_G}\right)^2 + 0.0193\left(\frac{P_B}{P_G}\right)^3,$$

where $P_G$ is the measured intensity of green light in the stimulus and $P_B$ is the measured intensity of blue light when said flickering is minimized or eliminated.

8. The apparatus of claim 7, wherein the numerical coefficients are adjusted to be consistent with the spectral properties of the specific blue and green LEDs and photodetector used in the apparatus.

9. The apparatus of claim 7, wherein the equivalent age, a, of the lens is calculated from the equation:

$$a = 69.93 L_{425} - 5.4636.$$

10. The apparatus of claim 9, wherein the equivalent age of the lens is used to calculate a corrected value of the peak macular pigment optical density, $D_{460}$.

11. The apparatus of claim 1, wherein both stimuli are symmetric about a central point.

12. The apparatus of claim 11, wherein the two stimuli are circular and are concentric with each other.

13. The apparatus of claim 1, wherein the apparatus further includes background illumination means for providing a continuously illuminated background area that surrounds, and extends to the perimeter of, each stimulus.

14. The apparatus of claim 13, wherein said background is green, and the background illumination means comprises a second integrating sphere positioned in front of the first said integrating sphere and having two apertures through which an area of surface in the first integrating sphere is, in use, viewed.

15. The apparatus of claim 13, wherein, in use, the luminance of the background is substantially the same as that of the stimulus when flicker of the stimulus is minimized or eliminated.

16. The apparatus of claim 14, wherein the size of the stimulus is governed by aperture means between the two integrating spheres.

17. The apparatus of claim 16, wherein the aperture means comprises a small and a large aperture, each corresponding to a respective size of stimulus, and an aperture holder movable into either selected one of two possible positions, in each of which a respective aperture is in register with the apertures in the second sphere.

18. The apparatus of claim 17, wherein the aperture holder is rotatable and is connected by a rotary solenoid for moving the holder into and out of said position.

19. The apparatus of claim 17, wherein the front of the holder has a light scattering screen around the small and large apertures such that when either aperture is selected said screen provides part of the background that extends to the perimeter of either stimulus.

20. The apparatus of claim 19, wherein the front of the holder has a light scattering screen around both apertures, or a respective screen around each aperture, said screen or screens providing said part of the background when either aperture is selected.

21. The apparatus of claim 1, wherein the front hemisphere of the interior of the second integrating sphere is black.

22. The apparatus of claim 1, wherein the apparatus includes a data processor operable to calculate, from the intensity measurements taken using the large and small stimuli, the optical density of the macular pigment and wherein the processor is also programmed to calculate the lens optical density of said eye, using the intensity measurement of blue light obtained with the larger stimulus, and also an intensity measurement of green light with said stimulus.

* * * * *